United States Patent
Hu

(10) Patent No.: US 8,524,314 B2
(45) Date of Patent: Sep. 3, 2013

(54) TOUCH SCREEN WITH BACTERIA INHIBITION LAYER AND MANUFACTURING METHOD THEREOF

(75) Inventor: Chun-Min Hu, Keelung (TW)

(73) Assignee: TPK Touch Solutions Inc., Taipei (TW)

( * ) Notice: Subject to any disclaimer, the term of this patent is extended or adjusted under 35 U.S.C. 154(b) by 263 days.

(21) Appl. No.: 12/830,453

(22) Filed: Jul. 6, 2010

(65) Prior Publication Data

US 2010/0272919 A1  Oct. 28, 2010

Related U.S. Application Data

(63) Continuation of application No. 11/192,066, filed on Jul. 29, 2005, now abandoned.

(51) Int. Cl.
*B05D 5/12* (2006.01)
(52) U.S. Cl.
USPC ............................................... 427/108
(58) Field of Classification Search
None
See application file for complete search history.

(56) References Cited

U.S. PATENT DOCUMENTS

| 6,783,805 B2 * | 8/2004 | Siegel et al. | 427/384 |
| 2004/0071986 A1 * | 4/2004 | Shoshi et al. | 428/446 |
| 2004/0121077 A1 * | 6/2004 | Park et al. | 427/383.1 |

FOREIGN PATENT DOCUMENTS

| EP | 0942351 | * | 9/1999 |
| JP | 9316369 | | 12/1997 |
| JP | 11110133 A | | 4/1999 |
| JP | 2002019044 A | | 1/2002 |

* cited by examiner

*Primary Examiner* — Brian Gulledge
(74) *Attorney, Agent, or Firm* — Gokalp Bayramoglu; Anna Tsang

(57) ABSTRACT

The present invention is to provide a touch screen having a bacteria inhibition layer for prohibiting bacteria from growing thereon and a method for manufacturing the same comprising uniformly dispersing particles of nano metal material in a solution to be applied to a surface treatment so that the solution can have a concentration of 20 ppm to 500 ppm; evenly spray coating the solution on a screen of the touch screen; and subjecting the solution coated on the screen of the touch screen to a heat treatment until solvent in the solution is completely evaporated so that the particles of the nano metal material are densely adhered to the screen of the touch screen to form a bacteria inhibition layer thereon.

7 Claims, 1 Drawing Sheet

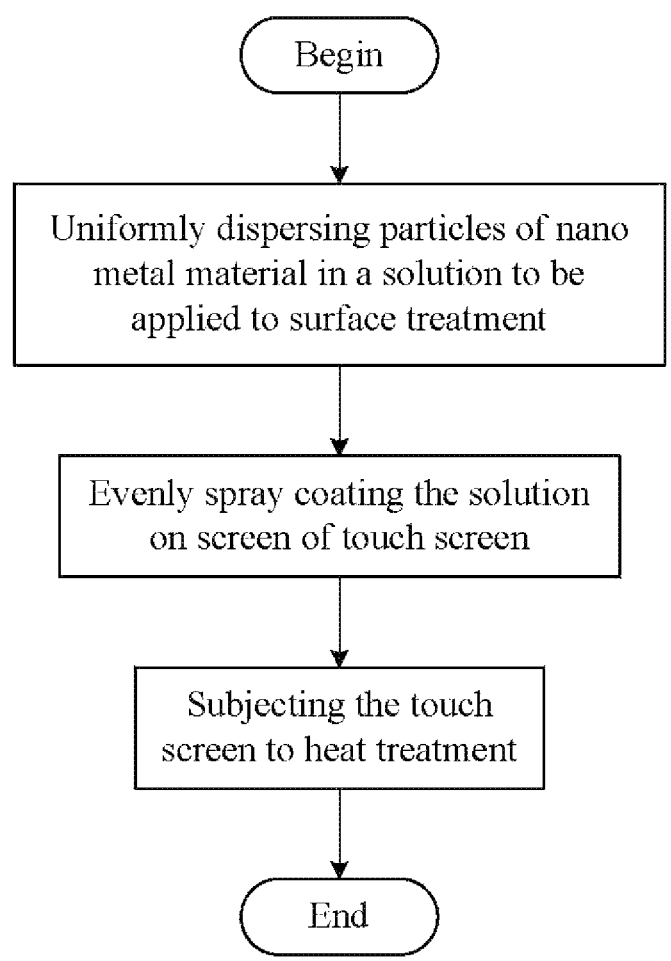

TOUCH SCREEN WITH BACTERIA INHIBITION LAYER AND MANUFACTURING METHOD THEREOF

This application is a continuation of Prior application Ser. No. 11/192,066, filed on Jul. 29, 2005.

FIELD OF THE INVENTION

The present invention relates to touch screens and more particularly to such a touch screen having a bacteria inhibition layer for prohibiting bacteria from growing thereon and a method for manufacturing the same.

BACKGROUND OF THE INVENTION

Electronics and computer technologies have made a significant progress in recent years due to booming of the Internet. Many compact, portable products are developed by electronic and computer product designers and manufacturers for fulfilling the urgent needs of vast consumers. Moreover, a number of significant, revolutionary modifications have been made with respect to input component or output component of any one of the products due to the consideration of user friendliness. The most important one of the modifications is the development of touch screen. In one aspect, a touch screen as a component of an electronic and computer product is adapted to show output characters or graphics thereon. In another aspect, the touch screen is adapted to send characters or instructions inputted by a user to the electronic and computer product. In other words, a touch screen serves as both input and output devices of an electronic and computer product. After viewing description or icons shown on a touch screen of an electronic and computer product, a user can point to things on it by touching a button or icon on the screen itself so as to operate the electronic and computer product. Thus, a user can not only use the electronic and computer product conveniently but also operate the same in a user friendly manner. For a software developer, the electronic and computer product provides a flexible, interactive operating platform in developing software with user friendly feature. For a consumer, no additional input device is required to install in the electronic and computer product. Thus, expense for buying an input device is saved and there is no need of preserving space on the electronic and computer product.

Recently, many types of electronic and computer products with touch screen are widely installed in public places such as schools, department stores, hospitals, airports, and railroad stations. Any person thus can touch the screen of a touch screen for information inquiry and guide. For users, touch screen is an input device with simple operation and user friendly features. Moreover, most problems encountered by people in public places can be solved successfully if software installed in a touch screen is well designed. However, bacteria may grow on the touch screen of an electronic and computer product since it is installed in a public place for user operation by touching the screen. This is a great threat to hygiene and public health. Thus, how to maintain a clean touch screen of one of many types of electronic and computer products installed in public places is a critical, important issue for authority of each public place.

In view of the fact that touch screens have become medium of disseminating bacteria thus for solving this problem many designers and manufacturers of electronic and computer products have developed a touch screen with bacteria inhibition feature in which a bacteria inhibition layer is coated on the touch screen. Typically, the bacteria inhibition layer is formed of organic material as implemented by designers and manufacturers of electronic and computer products. Organic material coated on a touch screen can inhibit growth of bacteria. However, organic material has a low melting point or boiling point and is easy to evaporate or decompose. Thus, its bacteria inhibition capability only lasts for a short period of time. Moreover, generally speaking, organic material is toxic. Hence, it is not appropriate to coat organic material on a product designed to be touched by users. Recently, still some manufacturers of the art employ popular titanium dioxide as optical catalyst for inhibiting growth of bacteria or even destroying the same. Titanium dioxide is subjected to UV (ultraviolet)-light for being catalyzed and thus for destroying bacteria. However, UV-light is very weak in a room environment. Thus, the desired bacteria inhibition effect is substantially compromised.

Thus, it is desirable to choose a suitable bacteria inhibition material and provide a novel process of manufacturing touch screens with a bacteria inhibition layer in order to contribute significantly to the advancement of the art.

SUMMARY OF THE INVENTION

After considerable research and experimentation, a touch screen with bacteria inhibition layer and manufacturing method thereof according to the present invention have been devised so as to overcome the above drawback of the prior art.

It is an object of the present invention to provide a method for manufacturing a touch screen comprising uniformly dispersing particles of nano metal material in a solution to be applied to a surface treatment so that the solution can have a concentration of 20 ppm to 500 ppm; evenly spray coating the solution on a screen of the touch screen; and subjecting the solution coated on the screen of the touch screen to a heat treatment until solvent in the solution is completely evaporated so that the particles of the nano metal material are densely adhered to the screen of the touch screen to form a bacteria inhibition layer thereon.

It is another object of the present invention to subject a screen of a typical touch screen (e.g., IR touch screen, resistive touch screen, capacitive touch screen, or ultrasonic touch screen) to be touched by users to a prior surface treatment (e.g., hardening treatment, endurability treatment, anti-glare treatment, or anti-reflection treatment) and a process of the present invention comprises uniformly dispersing particles of nano metal material in a solution to be applied to the surface treatment so that the solution can have a concentration of 20 ppm to 500 ppm; evenly spray coating the solution on the screen of the touch screen; and subjecting the solution coated on the screen of the touch screen to a heat treatment until the particles of the nano metal material contained are densely adhered to the screen of the touch screen to form a bacteria inhibition layer thereon.

It is still another object of the present invention to, in preparing the solution, employ a milling method or an ultrasonic method to uniformly disperse the particles of the nano metal material in the solution to be applied to the surface treatment.

It is yet another object of the present invention to employ a spin coating, a dipping coating, a spray coating, or a rolling coating to evenly spray coating the solution on the screen of the touch screen.

It is a further object of the present invention to, in a case of a substrate for the touch screen being organic material (e.g., PET film), provide the solution for the surface treatment including UV-light resin or thermosetting resin and appropriate solvent such that after evenly spray coating the solution on a surface of the PET film, it is subjected to UV lamp radiation or heat treatment depending on types of resin being used wherein the heat treatment is done in a relative low temperature, for example, between about 50° C. and 100° C.

It is a yet further object of the present invention to, in a case of a substrate for the touch screen being inorganic material (e.g., glass), provide the solution for the surface treatment including silicate (ester), water, acid, and appropriate solvent such that after evenly spray coating the solution on a surface of the glass, it is subjected to heat treatment wherein the heat treatment is done in a relative high temperature, for example, between about 160° C. and 200° C.

The above and other objects, features and advantages of the present invention will become apparent from the following detailed description taken with the accompanying drawings.

BRIEF DESCRIPTION OF THE DRAWINGS

FIG. 1 is a flowchart depicting a process for manufacturing touch screen with bacteria inhibition layer according to the invention.

DETAILED DESCRIPTION OF THE PREFERRED EMBODIMENTS

Referring to FIG. 1, a process for manufacturing touch screen with a bacteria inhibition layer in accordance with the invention is illustrated. The process comprises uniformly dispersing particles of nano metal material having a diameter in the range of about 1 nm to 100 nm in a solution to be applied to surface treatment so that the solution can have a concentration of 20 ppm to 500 ppm; evenly spray coating the solution on a screen of a touch screen; and subjecting the solution coated on the touch screen to a heat treatment until solvent in the solution is completely evaporated. As such, particles of nano metal material are densely adhered to the screen of touch screen to form a bacteria inhibition layer thereon. As a result, a touch screen with a bacteria inhibition layer is produced. Nano metal material as defined by the invention means that one has biochemical activation, is able to penetrate cell membrane of a bacteria for damaging enzyme and killing the same naturally, and has particles having a diameter in the range of about 1 nm to 100 nm. Nano metal material may be selected from nano gold (Au), nano silver (Ag), nano copper (Cu), nano zinc (Zn), nano platinum (Pt), or a combination or compound thereof such as nano silver oxide, nano copper oxide, nano zinc oxide, nano silver nitrate, nano copper nitrate, or nano zinc nitrate.

In the invention, the touch screen can be an infrared (IR) one, resistive one, capacitive one, or ultrasonic one depending on manufacturing process and construction. Screen of the touch screen to be touched by users is subjected to an appropriate surface treatment depending on applications. For example, surface treatment can be a hardening treatment, endurability treatment, anti-glare treatment, or anti-reflection treatment. In the invention the process comprises uniformly dispersing particles of nano metal material in a solution to be applied to surface treatment so that the solution can have a concentration of 20 ppm to 500 ppm. Next, the process comprises evenly spray coating the solution on a screen of a touch screen by employing a conventional coating method such as spin coating, dipping coating, spray coating, or rolling coating. Next, the process comprises subjecting the solution coated on the touch screen to a heat treatment until solvent in the solution is completely evaporated. As such, particles of nano metal material contained in the solution are densely adhered to the screen of touch screen to form a bacteria inhibition layer thereon. As a result, a touch screen with a bacteria inhibition layer is produced. In the step of preparing the solution, a milling method or ultrasonic method can be employed to uniformly disperse particles of nano metal material in the solution.

Conventionally, substrate for manufacturing the touch screen can be classified as organic compound and inorganic compound based on properties of material. For the former, it typically is PET (polyethylene terephthalate) film. For the latter, it typically is glass. Solution for surface treatment and subsequent processes are also different between the above two different substrates as contemplated by the invention. In a case of substrate for touch screen being PET film, solution for surface treatment comprises UV-light (or thermosetting) resin and appropriate solvent. After evenly spray coating the solution on a surface of PET film, it is subjected to UV lamp radiation or heat treatment depending on types of resin being used in which the heat treatment is done in a relative low temperature, for example, between about 50° C. and 100° C. In a case of substrate for touch screen being glass, solution for surface treatment comprises silicate (ester), water, acid, and appropriate solvent. After evenly spray coating the solution on a surface of glass, it is subjected to heat treatment only in which the heat treatment is done in a relative high temperature, for example, between about 160° C. and 200° C.

A couple of embodiments will be described in detail below for fully describing design spirit and operating principle of the invention as contemplated by the present inventor. Also, an experiment is conducted with respect to the produced touch screen so as to fully demonstrate bacteria inhibition or destroying effect of the invention.

In a preferred embodiment of the invention, a touch screen having glass as substrate is subjected to an anti-glare treatment including subjecting particles of nano silver having a diameter in the range of about 1 nm to 100 nm to an ultrasonic oscillation in a frequency ranged from 10 KHz to 50 KHz for uniformly dispersing the particles of primary state in an alcoholic solution for preparing a required dispersing solution; pouring an anti-glare treatment solution consisting of silicate (ester) compound and alcohol (or other appropriate solvent) into the dispersing solution; agitating the solution for at least 10 minutes until it is uniformly mixed with a pH value indicating acidity and the particles of nano silver having a concentration of about 20 ppm to 500 ppm; evenly spray coating the solution on a screen of a touch screen; and subjecting screen of the touch screen to a heat treatment in a temperature ranged from about 160° C. to 200° C. for about 30 minutes to 60 minutes until solvent in the solution is completely evaporated with the sol-gel reaction being completed. As such, an anti-glare layer with bacteria inhibition effect is formed on the touch screen. The anti-glare layer comprises silicone dioxide and nano silver and preferably has a thickness between about 50 and 5000 angstrom.

In the above embodiment in a case of the touch screen being IR touch screen, it is possible of uniformly dispersing particles of nano silver weighted 0.1 g and having a diameter of about 10 nm in ethyl alcohol weighted 100 g for preparing a required dispersing solution; adding ethyl silicate weighted 900 g in the dispersing solution; pouring the dispersing solution into an anti-glare treatment solution to uniformly mix them until the solution with a pH value 4 is prepared; evenly spray coating the solution on a glass screen of an IR touch screen; and subjecting the IR touch screen to a heat treatment in a predetermined temperature such as about 180° C. preferably for about 1 hour until an anti-glare layer with bacteria inhibition effect having a thickness of about 1000 angstrom is formed on the IR touch screen. In an experiment conducted by the present inventor for comparing the produced IR touch screen of the invention with a prior IR touch screen without being subjected to a bacteria inhibition process, *Escherichia coli* (*E. coli*) having a density of 1 million per square centimeter is disseminated on the screen of each of the above touch screens. The number of *E. coli* living on the screen of each of the above touch screens is counted after 24 hours. A result shows that the number of *E. coli* still living on the IR touch screen of the invention is about 99% less than the that at beginning of the experiment (i.e., 99% reduction). As comparison, the number of *E. coli* still living on the prior IR touch screen without being subjected to a bacteria inhibition process is about the same as that at beginning of the experiment. In conclusion, the touch screen of the invention can effectively inhibit the growth of bacteria thereon.

In another preferred embodiment of the invention in a case of the touch screen being a resistive one having its substrate formed of PET film, in a hardening treatment it is possible of uniformly dispersing particles of nano silver weighted 0.1 g and having a diameter of about 10 nm in methyl ethyl ketone weighted 100 g for preparing a required dispersing solution; adding an UV hardener mainly consisting of polybutene acrylate monomers weighted 900 g in the dispersing solution; uniformly mixing them; evenly spray coating the solution on screen of the resistive touch screen; subjecting the screen of the resistive touch screen to an IR heating for about 5 minutes until solvent in the solution is completely evaporated; and subjecting the resistive touch screen to be radiated by a UV lamp having a power of 40 W to 60 W until a hardened layer with bacteria inhibition capability having a thickness of about several micrometers is formed on the resistive touch screen (i.e., hardening treatment finished). In an experiment conducted by the present inventor for comparing the produced resistive touch screen of the invention with a prior resistive touch screen without being subjected to a bacteria inhibition process, *E. coli* having a density of 1 million per square centimeter is disseminated on the screen of each of the above touch screens. The number of *E. coli* living on the screen of each of the above touch screens is counted after 24 hours. A result shows that the number of *E. coli* still living on the resistive touch screen of the invention is about 99% less than that at beginning of the experiment (i.e., 99% reduction). As comparison, the number of *E. coli* still living on the prior resistive touch screen without being subjected to a bacteria inhibition process is about the same as that at beginning of the experiment. In conclusion, the touch screen of the invention can effectively inhibit the growth of bacteria thereon.

While the invention herein disclosed has been described by means of specific embodiments, numerous modifications and variations could be made thereto by those skilled in the art without departing from the scope and spirit of the invention set forth in the claims.

What is claimed is:

1. A method for manufacturing a touch screen having an inorganic substrate with a bacteria inhibition layer, the method comprising:
    forming a dispersing solution by uniformly dispersing particles of nano-sized metal material in a solvent, the nano-sized metal material being nano-sized silver (Ag);
    mixing the dispersing solution with an anti-glare treatment solution which comprises silicate, water, acid and solvent to forum an acid solution so that the acid solution has a concentration of 20 ppm to 500 ppm of nano-sized metal material;
    evenly coating the acid solution on a surface of the inorganic substrate of the touch screen; and
    performing a heat treatment to the inorganic substrate at a temperature ranged from 160° C. to 200° C. until the solvent in the acid solution is completely evaporated so that the particles of the nano-sized metal material are densely adhered to the surface of the inorganic substrate of the touch screen to form a bacteria inhibition layer thereon, wherein, the bacteria inhibition layer has a thickness between 50 Å and 5000 Å.

2. The method of claim 1, wherein the inorganic substrate is a glass substrate.

3. The method of claim 1, wherein the solvent of the dispersing solution comprises an alcoholic solvent.

4. The method of claim 1, wherein the dispersing solution is subjected to a mixing technique comprising a milling method and an ultrasonic vibration method at a frequency ranged from 10 KHz to 50 KHz to uniformly disperse particles of the nano-sized material in the solvent.

5. The method of claim 1, wherein the acid solution is subjected to a spray coating, to coat on the surface of the inorganic substrate.

6. The method of claim 1, wherein the pH of the acid solution is brought to 4 in the step of mixing the dispersing solution and the anti-glare treatment solution.

7. The method of claim 1, wherein the heat treatment is performed at about 180° C. for about 1 hour.

* * * * *